(12) United States Patent
Balan et al.

(10) Patent No.: US 10,274,478 B2
(45) Date of Patent: Apr. 30, 2019

(54) ULTRA LOW CAPACITANCE GLASS SUPPORTED DIELECTRIC MEMBRANES FOR MACROMOLECULAR ANALYSIS

(71) Applicant: The Trustees of the University of Pennsylvania, Philadelphia, PA (US)

(72) Inventors: Adrian Balan, Paris (FR); Marija Drndic, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 76 days.

(21) Appl. No.: 15/448,776

(22) Filed: Mar. 3, 2017

(65) Prior Publication Data

US 2017/0254796 A1    Sep. 7, 2017

Related U.S. Application Data

(60) Provisional application No. 62/303,362, filed on Mar. 3, 2016.

(51) Int. Cl.
| | |
|---|---|
| *G01N 27/00* | (2006.01) |
| *G01N 33/487* | (2006.01) |
| *C03C 15/00* | (2006.01) |
| *C12Q 1/6869* | (2018.01) |
| *G01N 33/00* | (2006.01) |
| *C07B 59/00* | (2006.01) |

(52) U.S. Cl.
CPC ....... *G01N 33/48721* (2013.01); *C03C 15/00* (2013.01); *C12Q 1/6869* (2013.01); *C03C 2218/34* (2013.01)

(58) Field of Classification Search
CPC ............... G01N 27/00; G01N 27/3275; G01N 27/4145; G01N 33/5438; C07B 59/002; C07B 59/00

USPC ............ 422/82.01, 68.1, 50; 436/94, 93, 91
See application file for complete search history.

(56) References Cited

U.S. PATENT DOCUMENTS

2013/0309776 A1* 11/2013 Drndic .................. G01N 27/26 436/94

OTHER PUBLICATIONS

Balan et al, Suspended Solid-state Membranes on Glass Chips with Sub 1-pF Capacitance for Biomolecule Sensing Applications, Sci. Rep. 5, 17775; doi: 10.1038/srep17775 (2015). (Year: 2015).*
Balan et al, Supplemental Information: Suspended Solid-state Membranes on Glass Chips with Sub 1-pF Capacitance for Biomolecule Sensing Applications, Sci. Rep. 5, 17775; doi: 10.1038/srep17775 (2015). (Year: 2015).*

* cited by examiner

*Primary Examiner* — Christine T Mui
(74) *Attorney, Agent, or Firm* — Baker & Hostetler LLP

(57) ABSTRACT

Provided are suspended solid-state membranes on glass chips with improved capacitance. The membranes include a first cavity formed in the thickness of the glass membrane, the first cavity having a width that increases along the direction extending from the first surface of the membrane to the second surface of the membrane, a first membrane surmounting at least a portion of the first surface of the glass membrane, the first membrane having a pore formed therethrough, and the pore of the first membrane being in fluid communication with the first cavity of the glass membrane. Also provided are related methods of fabricating the disclosed chips and of using the disclosed chips for macromolecular analysis.

20 Claims, 21 Drawing Sheets
(16 of 21 Drawing Sheet(s) Filed in Color)

Initial structure
Fused Silica 100-400μm
100nm Si3N4 – both sides
150nm a-Si –both sides
Spin 10um SPR-2200 7 Photoresist Expose small (1um squaress in the photoresist), Hard bake
RIE Etch 4 min Ch4 (35sccm) +O2 (3sccm), 200W Plasma
Wet etch HF 49%

Wet etch process finishes after ~200min (1um /min etch rate)

Remove resist in Pirahna or Nanostrip
Remove a-Si in KOH (5min)
Eventually thin by RIE or STEM
Drill using TEM 2010F $$C = \varepsilon\, 2\pi R \left( \ln\left(\frac{L}{R}\right) - \ln\left(\left|\frac{L}{R} - 1\right|\right) \right)$$

ULTRA LOW CAPACITANCE GLASS SUPPORTED DIELECTRIC MEMBRANES FOR MACROMOLECULAR ANALYSIS

CROSS-REFERENCE TO RELATED APPLICATION

This application claims the benefit of and priority to U.S. Patent Application No. 62/303,362, "Ultra Low Capacitance Glass Supported Dielectric Membranes For Macromolecular Analysis" (filed Mar. 3, 2016), the entirety of which application is incorporated by reference herein for any and all purposes.

GOVERNMENT RIGHTS

This invention was made with government support under Grant Numbers R21HG004767 and R01HG006879 awarded by the National Institutes of Health. The government has certain rights in the invention.

TECHNICAL FIELD

The present disclosure relates to the field of glass nanoscale devices and to the field of biomolecular analysis.

BACKGROUND

Solid-state membranes have use in many applications in nanoelectronics and nanomedicine, from single molecule sensors to water filtration, and yet many of their electronics applications are limited by the relatively high current noise and low bandwidth. Accordingly, there is a need in the art for improved devices.

SUMMARY

In meeting these needs, provided is an integrated fabrication process to grow and define circular silicon nitride membranes on glass chips that successfully lower the chip capacitance to below 1 pF. One may use these devices for low noise, high-bandwidth DNA translocation measurements. One may also make use of this versatile, low capacitance platform to suspend other thin, two-dimensional membrane such as graphene.

Many personalized medicine, environmental, and mechanical applications require the use of membranes that could effectively and reliably separate two regions of empty space or fluids. Several thin membranes, sometimes as thin as one atom in the case of graphene, have proven impermeable to gas or fluid flow unless nanoholes are introduced into them. In the presence of nanoholes, molecular flow can be controllably driven through them and this flow is maximized as the membrane thickness is reduced, creating new opportunities for optimizing either the ionic current signals for genetic sequencing, the water flux for filtration and desalination, or the sensitivity to molecular structure in nanoscale devices exploiting freestanding thin membranes. Progress in the field has been fast, in large part thanks to the development of new experimental techniques that enable unprecedented control at the nanoscale to grow and place membranes at desired positions relative to a substrate. The past few years have witnessed significant results in developing such membranes and using them in applications ranging from mechanics to nanoelectronics and biomedicine.

In many biomedically-relevant nanoelectronics applications, it is advantageous that the overall capacitance of the membrane chip is small in order to minimize the electrical noise produced when the voltage noise from the power source couples to the total capacitance in the system. Frequently, the chip capacitance is the dominant capacitance and it governs the lowest current noise that can be achieved at a particular bandwidth. Specifically, this is important for the use of membranes for biomolecule detection, a class of applications attracting increasing interest and witnessing significant progress. Solid-state membrane devices with nanopores have been used for example to differentiate biomolecules such as proteins. DNA homopolymers and miRNA, to determine nanoparticle surface charges, or as nanoscale reactors for nanoparticle synthesis. However, the wide applicability of these results is limited by the noise in the ionic current signal. Several approaches have been explored to improve the signal-to-noise ratio, either by reducing the nanopore size and thickness, or by placing a nanoribbon next to the nanopore as a sensor.

In one aspect, the present disclosure provides macromolecule analysis chips, comprising: a glass membrane having a thickness defined between first and second surfaces of the glass membrane, the thickness being in the range of from about 10 micrometers to about 5000 micrometers, the glass membrane further having a first cavity formed in the thickness of the glass membrane, the first cavity having a width that increases along the direction extending from the first surface of the membrane to the second surface of the membrane, a first membrane surmounting at least a portion of the first surface of the glass membrane, the first membrane having a pore formed therethrough, and the pore of the first membrane being in fluid communication with the first cavity of the glass membrane.

Also provided are methods of fabricating an analysis chip, comprising: in a glass membrane having a thickness defined between first and second surfaces of the glass membrane, forming a first cavity in the glass membrane, the first cavity having a width that increases along the direction extending from the first surface of the membrane to the second surface of the membrane.

Further provided are methods, the methods comprising using a chip as described herein to perform structural analysis of a macromolecule.

BRIEF DESCRIPTION OF THE DRAWINGS

The file of this patent or application contains at least one drawing/photograph executed in color. Copies of this patent or patent application publication with color drawing(s)/photograph(s) will be provided by the Office upon request and payment of the necessary fee.

The foregoing summary, as well as the following detailed description of illustrative embodiments of the containment apparatus of the present application, will be better understood when read in conjunction with the appended drawings. For the purposes of illustrating the containment apparatus of the present application, there is shown in the drawings illustrative embodiments. It should be understood, however, that the application is not limited to the precise arrangements and instrumentalities shown. In the drawings.

DETAILED DESCRIPTION OF ILLUSTRATIVE EMBODIMENTS

Figure 1A:
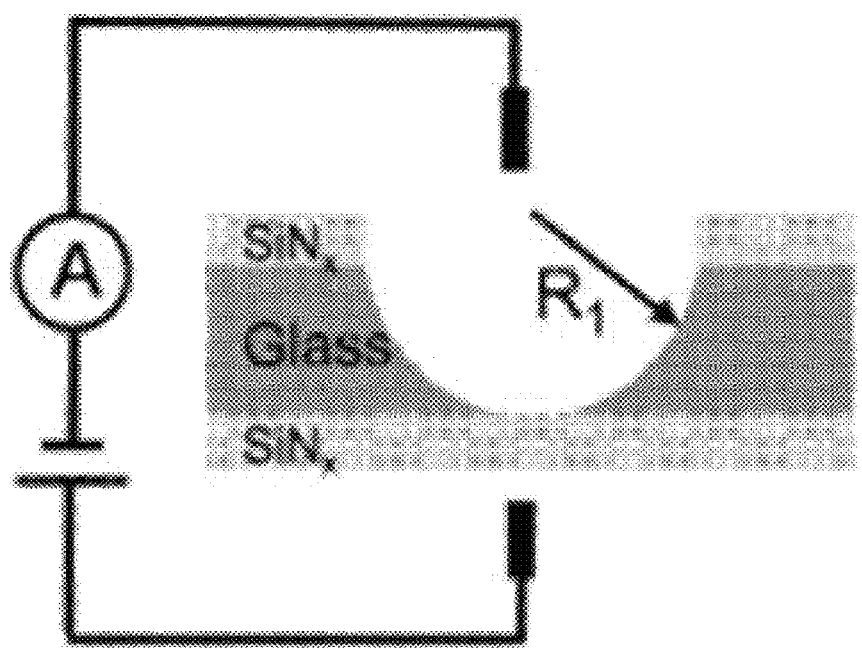
FIG. 1A provides a schematic of an exemplary glass chip according to the present disclosure.

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claimed subject matter. Also, as used in the specification including the appended claims, the singular forms "a," "an," and "the" include the plural, and reference to a particular numerical value includes at least that particular value, unless the context clearly dictates otherwise. The term "plurality," as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable. Additionally, unless specified otherwise, use of the word "substantially" herein is intended to mean considerable in extent or largely but not necessarily wholly that which is specified.

It is to be appreciated that certain features of the disclosed subject matter which are, for clarity, described herein in the context of separate embodiments, can also be provided in combination in a single embodiment. Conversely, various features of the disclosed subject matter that are, for brevity, described in the context of a single embodiment, can also be provided separately or in any subcombination. Further, reference to values stated in ranges includes each and every value within that range. Any documents cited herein are incorporated herein by reference in their entireties for any and all purposes.

Above 10 kHz frequency, the noise may largely result from the interaction between the amplifier's voltage noise and the chip capacitance. Irms, the root-mean-square input referred current noise, is given by the following equation:

$$I_{rms}(B) = \left(\frac{2\pi}{\sqrt{3}}\right) B^{3/2} (C_{chip} + C_w + C_{amp}) v'_n$$

Here, B is the bandwidth, vn is the input-referred voltage noise of the amplifier, Cchip is the chip capacitance, Cw is the capacitance of the wiring from the amplifier to the chip and Camp is the capacitance of the amplifier. Therefore, one major approach to improve the noise, and consequently the signal-to-noise ratio, is to reduce the chip capacitance. There have been several efforts to reduce the chip capacitance by bonding glass slides onto the silicon chip, or transferring silicon nitride membranes onto glass substrates. The thin silicon nitride membranes on glass chips reported here further reduce the chip capacitance to below what has been reported previously. The reported fabrication process is also transfer-free and therefore, chips can be made quickly and in large quantities. Further, these chips are amenable to the harsh acid or plasma treatments often used to make chips hydrophilic or to clean the chips for reuse between experiments.

This disclosure provides, inter alia, the design and fabrication of chips consisting of suspended silicon nitride membranes spanning over apertures on glass substrates. A number of chip designs are provided, including a simple chip design that results in sub-2 pF capacitances, and a two-step fabrication design resulting in sub-1 pF capacitance chips. This technology replaces the conventional silicon substrate, which substrate contributes to most of the device capacitance with an insulating glass substrate.

The resulting total chip capacitance below 1 pF leads to an improved noise performance in ionic current signals that one may illustrate by low noise DNA translocation experiments, paving the way to more sensitive measurements for biomolecules detection and differentiation. The fabrication process for silicon nitride membranes on glass reported here is transfer-free and suitable for large-scale production. Also demonstrated is the use of this platform to suspend other 2D materials (graphene) on top of holes in silicon nitride membrane that are in turn suspended across the aperture.

Exemplary Results

FIG. 1A provides an exemplary measurement setup for the disclosed low-capacitance devices in electrolyte solution. In this exemplary setup, a silicon nitride membrane is supported by a glass chip, 5 mm×5 mm wide and 200-500 μm thick. Typically a voltage up to 1 V is applied across the membrane with an amplifier (Chimera Instruments, New York, N.Y.) to drive the analytes in solution to interact with the membrane or pass through the nanopore.

Figure 1B:
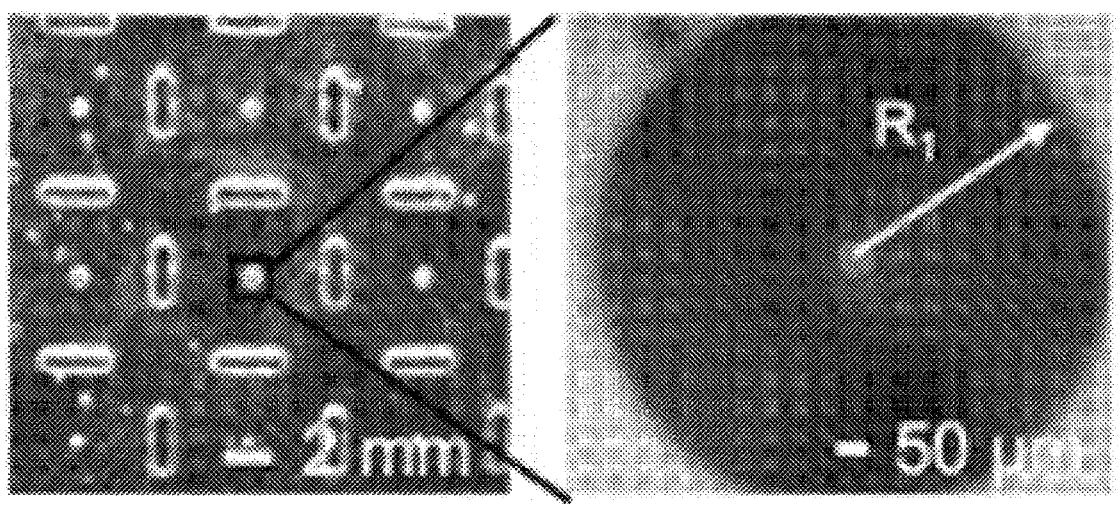
FIG. 1B provides an optical image of the glass wafer of FIG. 1A.
Figure 1C:
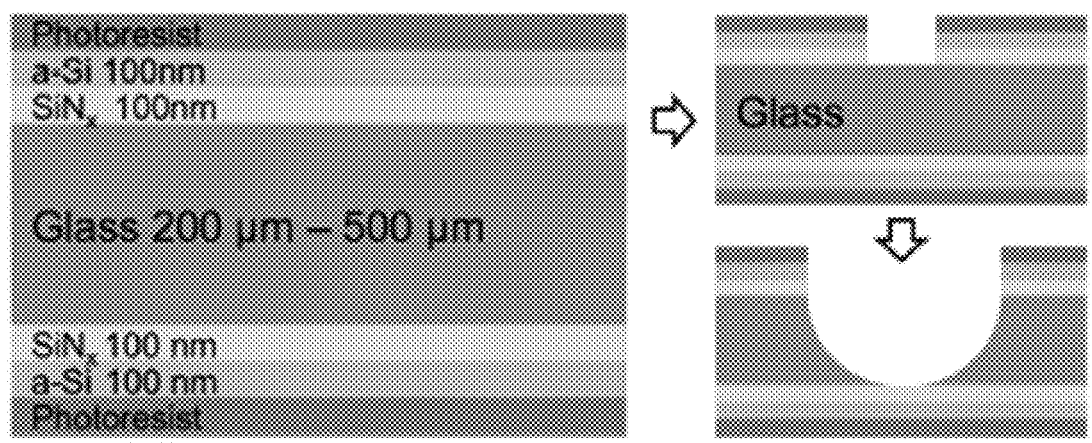
FIG. 1C provides a schematic of the glass and the membrane manufacturing process for the device of FIG. 1A and FIG. 1B.

By measuring the resulting current variations, nanopores have been shown to differentiate biomolecules with various sizes, structures, and charges. Two images of glass chips at different magnifications are shown in FIG. 1B and FIG. 1C. FIG. 1C shows a silicon nitride (SiNx) membrane suspended across a central aperture, several micrometers in size, where glass is etched away.

FIG. 1D demonstrates the fabrication process of the SiNx membranes on glass chips. On both sides of the glass wafer, a LPCVD technique was used to deposit a layer of 100-nm-thick SiNx as the membrane material and 100-nm-thick amorphous Si (a-Si) layer on top of SiNx as a protection against the hydrogen fluoride (HF) etch later in the process. It should be understood that a-Si is illustrative, and is not the only material that might be used to protect against the etching process. Further, a protecting material may not always be necessary.

The glass used in this exemplary study was fused silica, which has a comparatively high softening point, allowing the LPCVD process for high quality SiNx membranes. SPR-220 photoresist was spin-coated on both sides, and photolithography squares of 10 μm in size were patterned. Etching away of the a-Si and SiNx layers was done by $CF_4$ reactive ion etching.

The glass substrate was etched in a 49% HF solution until the sphere created by isotropic etching reached the bottom SiNx layer. The remaining photoresist and a-Si are stripped away by acetone and KOH respectively, resulting in a final glass chip with a silicon nitride membrane suspended at its center.

Figure 2A:
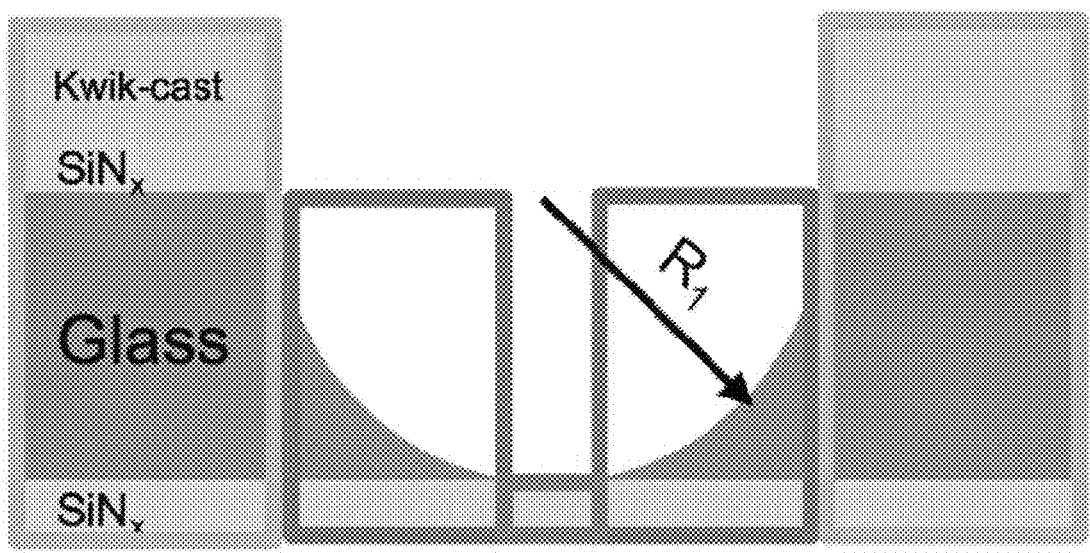
FIG. 2A provides a schematic of a glass chip with silicon nitride membrane in the center, with an silicone elastomer (e.g., Kiwk-Cast™) applied on top as insulation.

In order to estimate the total capacitance of the resulting glass chip, one may (without being bound to any particular theory) represent the glass chip as a set of individual capacitive elements and calculate each capacitance contribution to the total chip capacitance as shown in the coded regions shown in FIG. 2A.

Figure 2B:
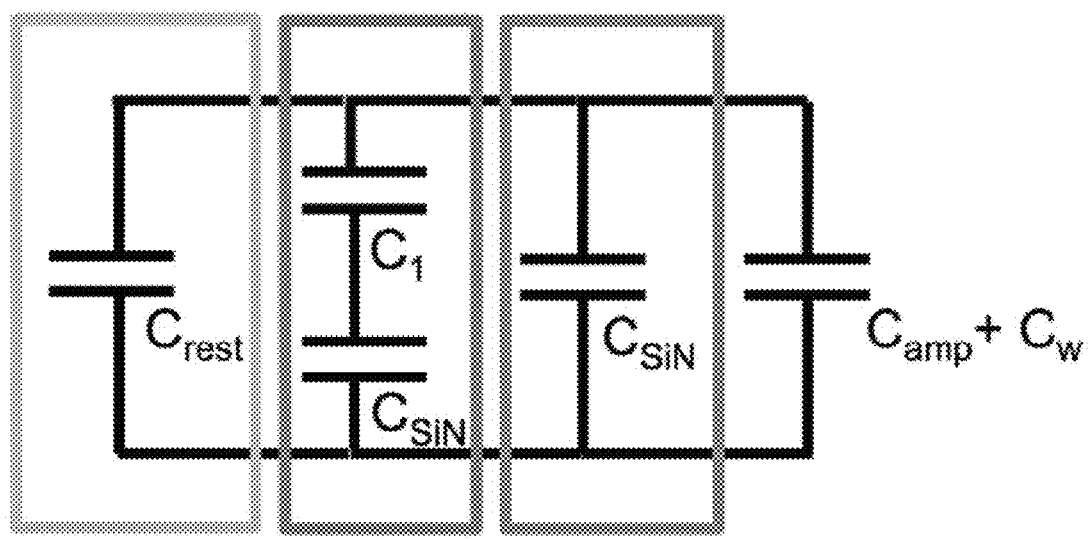
FIG. 2B provides a corresponding circuit diagram for the device of FIG. 2A.

Each identified area represents parallel capacitors and could be summarized by a circuit diagram as shown in FIG. 2B. The right-hand boxed area is the freestanding SiNx membrane with capacitance Cmem. The middle boxed area is the area where the glass substrate was etched away isotropically, creating a hemispherical structure. The capacitance in this area is estimated by integrating infinitesimal parallel plates over the whole sphere area and is given by the equation:

$$C_1 \sim 2\pi\varepsilon R_1 \left[\ln\left(1 + \frac{R_1}{t}\right)\right]$$

where R1 is the thickness of the glass chip and also the radius of the sphere, t is the thickness of the SiNx layer, and _ is the permittivity of glass. The left-hand boxed area is the remaining area of the chip covered by a layer of silicone elastomer (Kwik-Cast™, World Precision Instruments), used as a seal to separate the two chambers of electrolyte solutions, and its capacitance is noted as Crest. The estimated total chip capacitance is summed up to be Cmem+C1+Crest.

Figure 2C:
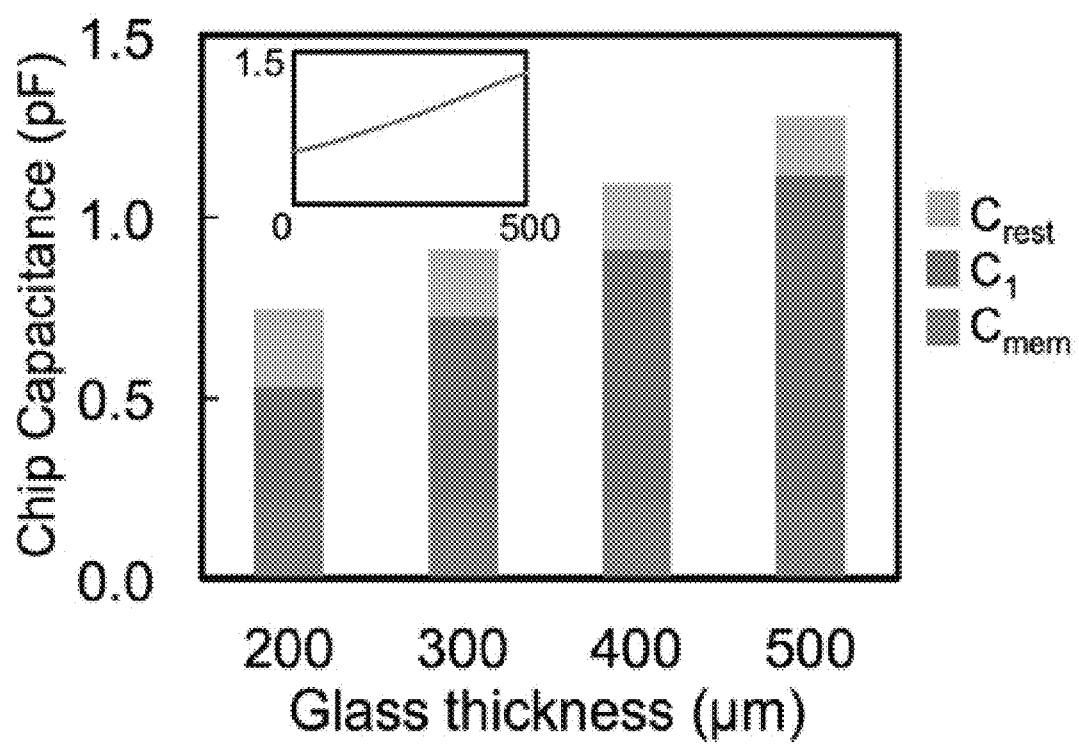
FIG. 2C provides a bar graph of chip capacitance for exemplary glass thickness values of 200, 300, 400, and 500 μm, showing relative contributions from regions $C_{rest}$, $C_1$ and $C_{mem}$, and the inset is the minimum capacitance as a function of glass thickness, with the units in the inset being the same as in the main FIG. 2C.

FIG. 2c summarizes the results of the estimated total chip capacitance with glass thickness of 200 μm to 500 μm. Here was assumed a membrane radius of 10 μm, with 0.5 mm Kwik-cast applied around the etched sphere, and an electrolyte solution droplet covering an area ~7 mm² (1.5 mm radius of circular area coverage) serving as electrolyte chamber. Glass chips designed by this method can reach capacitances below 1 pF for glass thickness below 300 μm. Again without being bound to any particular theory, the relatively large contribution to the overall capacitance comes from the boxed area in FIG. 2D where the dielectric layer is the thinnest.

Figure 2D:
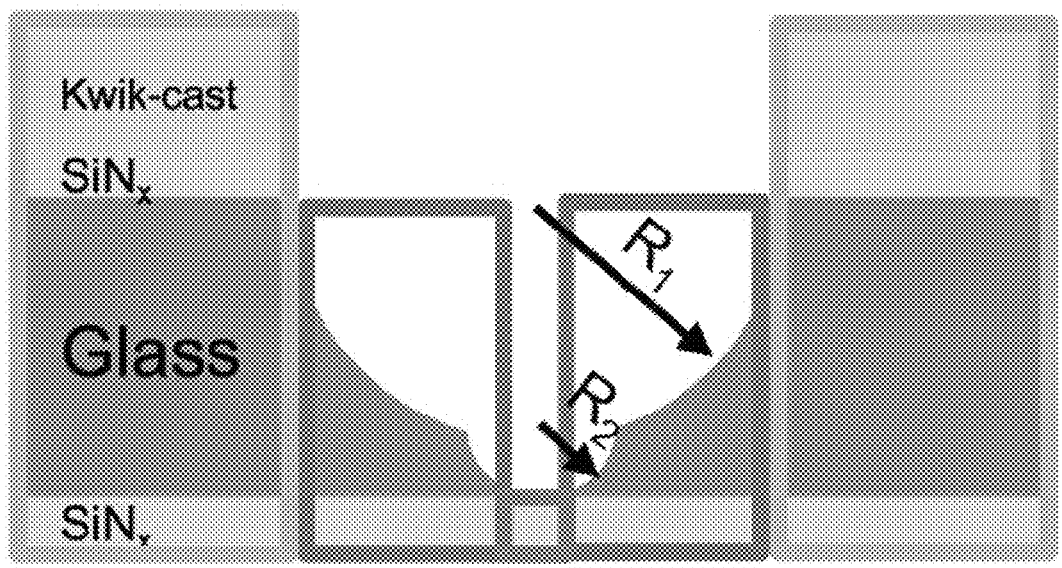
FIG. 2D provides a schematic of a glass chip device produced by a two-step etching that gives rise to first and second cavities formed in the glass substrate.
Figure 2E:
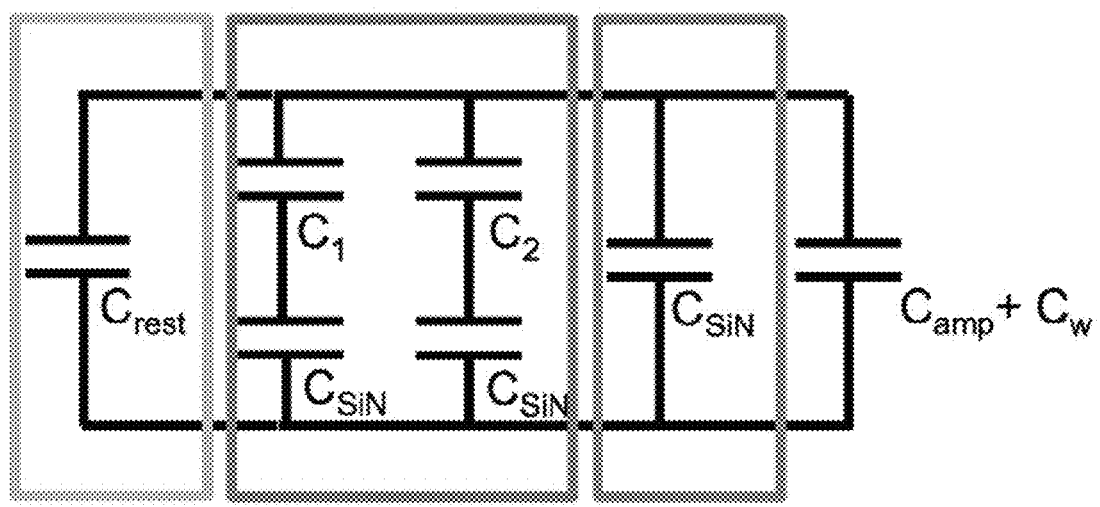
FIG. 2E provides a corresponding capacitor circuit diagram for the device of FIG. 2D.
Figure 2F:
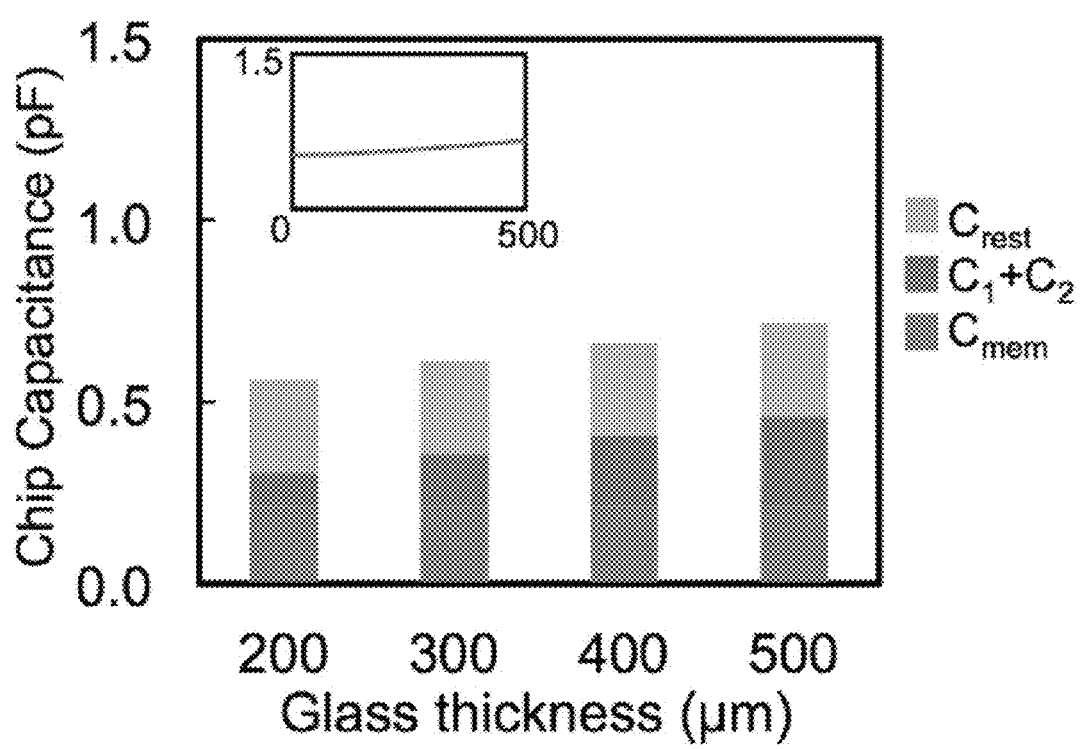
FIG. 2F provides a bar graph of the chip capacitance for glass thicknesses of 200, 300, 400, and 500 μm, respectively, showing relative contributions from the boxed regions in FIG. 2E (the inset is the minimum capacitance as a function of glass thickness, and the units are the same as the main FIG. 2F)
Figure 8:
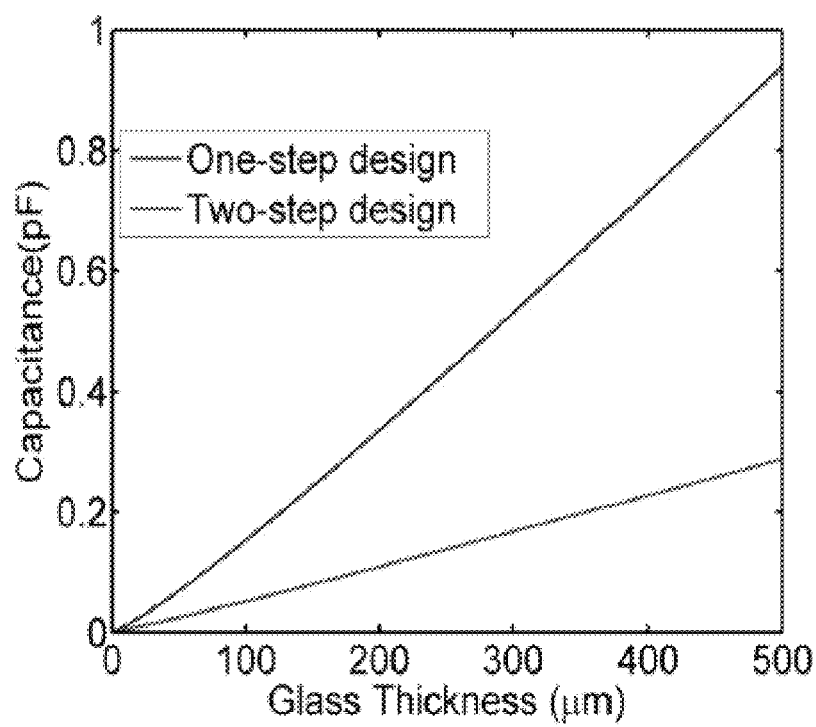
FIG. 8 provides a comparison of the minimal capacitance as a function of the device thickness for the spherical part for the two designs of FIG. 2A and FIG. 2D.

In order to further modulate the total chip capacitance, one may incorporate a two-step etching method, obtaining the chip structure shown in FIG. 2D. One difference between the two designs is that in this two-step etching process, there are now two etched spherical cavities stacked on top of each other and in fluid communication with one another. The capacitance contribution of the red area is now given by $$C_1 + C_2 \sim 2\pi\varepsilon R_1 \left[\ln\left(1 + \frac{R_1}{t + R_2}\right)\right] + 2\pi\varepsilon R_2 \left[\ln\left(1 + \frac{R_2}{t}\right)\right]$$

where R1 is the radius of the upper sphere, and R2 is the radius of the lower sphere. The sum of the radii of the two spheres is equal to the total thickness of the chip. The capacitor circuit diagram of this chip design is shown in FIG. 2E. With this chip design, the theoretical minimum of the total chip capacitance for glass in the 200-500 μm thickness range could be reduced by approximately 0.5 pF, as compared to that of chips produced by a one-step etching. In this case, the contribution from the red area where the glass is etched away in a spherical shape is greatly reduced (FIG. 2F and FIG. 8).

This reduction in capacitance is due to a thicker insulating glass layer remaining in the chip. It is useful to estimate the capacitance minimum as a function of the device thickness as shown in the inset of FIGS. 2C and 2F. In both designs, the capacitance asymptotically approaches a minimum value of 0.5 pF given by the large Kwik-cast covered area when the glass thickness and sphere radius approaches zero. However, the capacitance of the two-step etching design is less sensitive to the membrane thickness, allowing one to use more robust 300 μm glass chips.

Realizing nanopores in ultrathin membranes is particularly important for two reasons: to maximize the ionic current signal level (by minimizing the nanopore thickness and therefore its resistance), and to maximize the spatial sensitivity (in order to sample a small part of the molecule, such as a single DNA base). One straightforward approach to realize ultrathin membranes would be to thin the SiNx membrane by reactive-ion etching or STEM thinning, e.g., to a thickness of a-Si of about 1 nm.

Alternatively, one may use these glass chips as a more general platform to suspend 2D materials such as graphene (3.4 A thick) and metal dichalcogenides ($MoS_2$, $WS_2$~6 A thick) monolayer membranes. 2D materials, due to their atomic-level thickness, are suitable biomolecule sensors. The low capacitance SiNx-on-glass platform shown in FIG. 1A further enhances the sensing capabilities of such 2D materials.

Figure 3A:
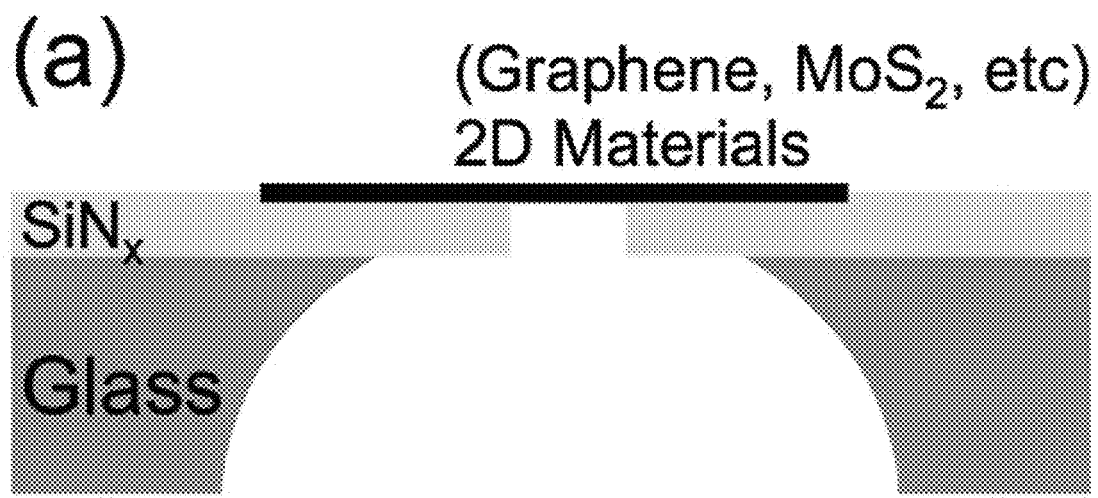
FIG. 3A provides an illustration of using 2D materials, such as graphene or MoS2, on a membrane-on-glass chip.
Figure 3B:
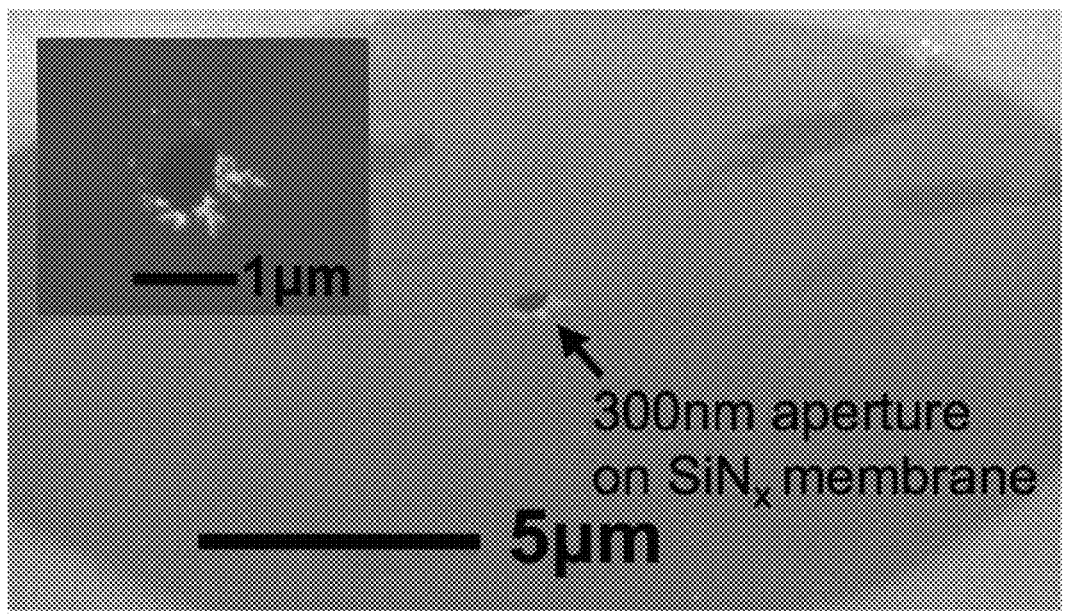
FIG. 3B provides a SEM image of a graphene sheet covering the 300-nm-large aperture in a suspended SiNx membrane.

FIG. 3A is a schematic illustrating a 2D membrane suspended over a ~300-nm-size aperture formed in the SiNx membrane over the glass chip. One example is the scanning electron microscope (SEM) image of a graphene sheet suspended in this fashion (FIG. 3B).

The 300-nm-size aperture in the SiNx membrane was first fabricated by electron beam lithography and plasma etching. CVD grown graphene characterized by Raman spectroscopy was then transferred onto the membrane over the aperture. The device is placed into electrolyte solution as shown in FIG. 1A, and when bias voltage is applied the current flowing through is nearly zero suggesting complete graphene coverage over the aperture. In principle, other 2D materials, such as metal dichalcogenides monolayer membranes could be transferred onto this SiNx-on-glass platform as typically transferred onto Si substrate.

Figure 4A:
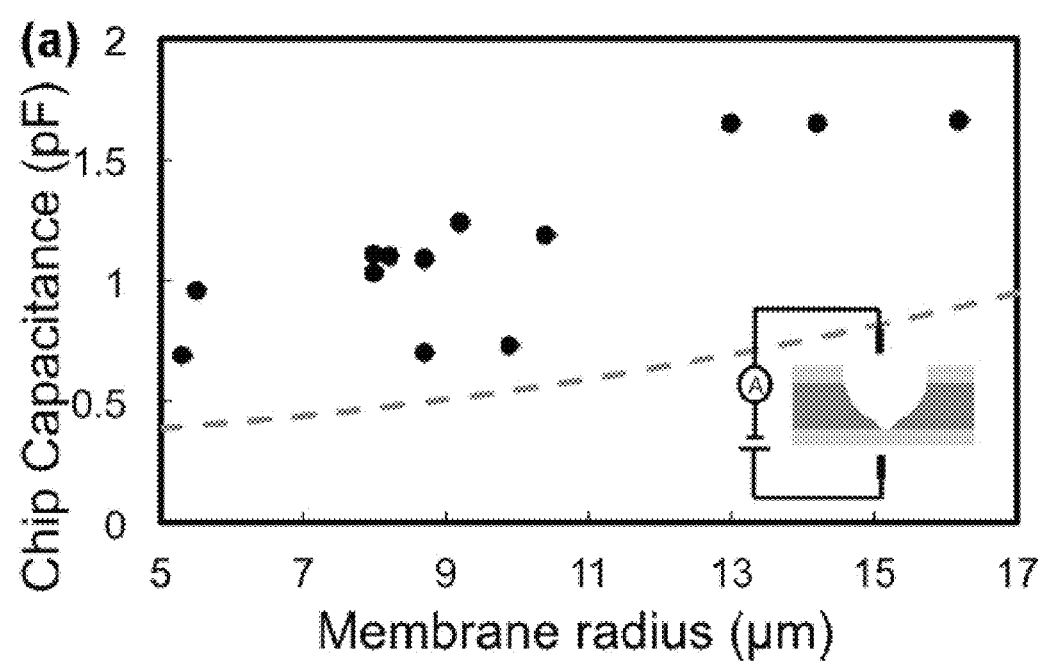
FIG. 4A provides the measured capacitance, Cchip, of exemplary glass chips produced by two-step etching (FIG. 2D) as a function of SiNx membrane radius (μm)

Measured chip capacitance, Cchip, for 13 devices are summarized in FIG. 4A as solid circles, and the dashed blue line is the estimated minimum attainable capacitance. The chips are made with fused silica of thickness 300 μm and SiNx membrane thickness 100 nm, fabricated by the two-step etching method described previously. Chip capacitance was measured by applying triangular-wave voltage pulses with a Chimera amplifier and measuring current versus time in a fluidic cell as shown in FIG. 1A. For membranes with radii smaller than 10 μm, one may experimentally attain $C_{chip}$ in the sub-1 pF regime, and $C_{chip}$ scales with the membrane radius in accordance with estimation.

Figure 4B:
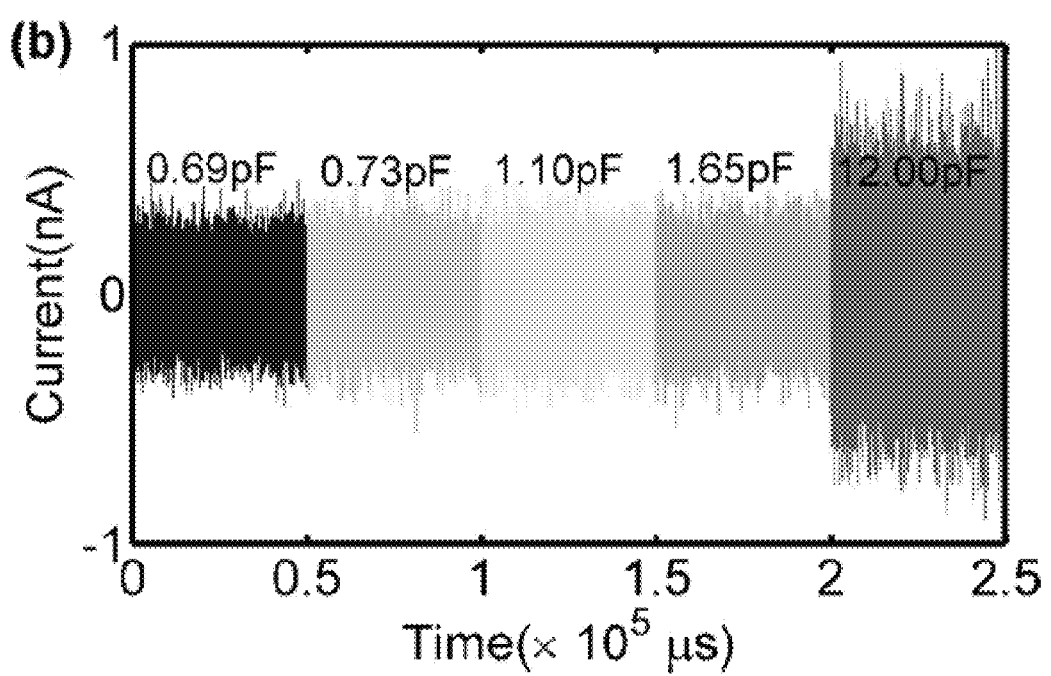
FIG. 4B provides measured ion current temporal traces for several glass chips with capacitances Cchip=0.69, 0.73, 1.1 pF, and 1.65 pF showing an amplifier-limited noise.

When the capacitance of chips is on the same order of the internal amplifier capacitance (~20 pF), one may observe the contribution of the chip capacitance to the current noise (here shown for a 12 pF device in FIG. 4B). As the capacitances of these glass chips are much lower than the amplifier internal capacitance, the resulting ionic current noise observed for these chips shown in FIG. 3B is undistinguishable from the open-headstage noise (~110 pArms). In other words, in this case the noise is dominated by the amplifier. The silicon nitride membrane chips demonstrated here are suitable for applications requiring low capacitances, including the realization of nanopores for biomolecule analysis and DNA sequencing.

Figure 4C:
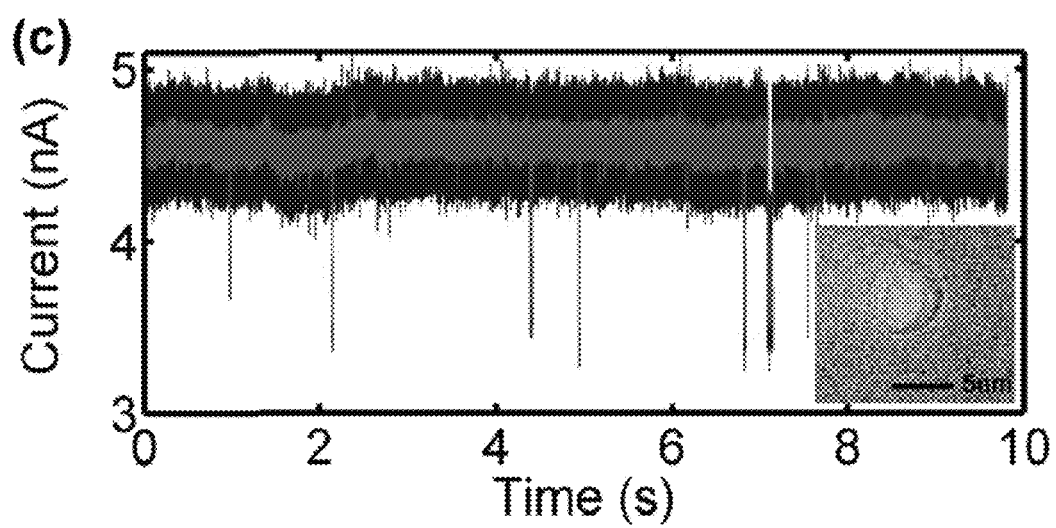
FIG. 4C provides a current vs. time trace of 3 kbp (kilo base pairs) dsDNA segments translocating through one of the devices.
Figure 4D:
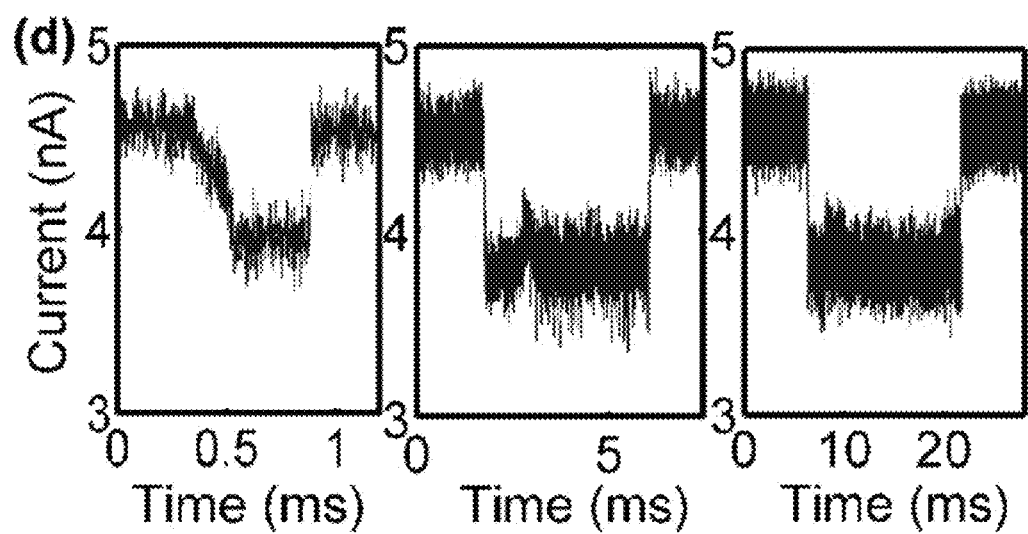
FIG. 4D provides details of events recorded with the disclosed devices having lengths from 0.5 ms to 10 ms from FIG. 3D.

One may use these devices to demonstrate very low noise translocations of 3 kbp double-stranded (ds) DNA. Nanopores can be drilled, for example, with a focused electron beam in transmission electron microscope (TEM) or by controlled dielectric breakdown. A TEM image of a nanopore drilled by focused electron beam on 100 nm thick SiNx membrane is shown in the inset of FIG. 4C. FIG. 4C shows an ionic current versus time trace of translocation events measured at 1 MHz (blue trace, above and below white lines) and filtered at 100 kHz (red trace, between white lines) for 1 V bias voltage, and FIG. 4D shows details of events with lengths from 0.5 ms to 10 ms. The total noise compares favorably to previous measurements at the same frequency, despite the higher applied voltage. Also, using these low capacitance chips and a high frequency amplifier one may detect small (180 bases), single stranded DNA segments with better noise characteristics than in previous studies.

Exemplary Methods

Device Fabrication

The 4 inch glass wafer comprised fused silica thickness of 200-500 um, and SiNx thickness of 100 nm was deposited on both sides with LPCVD. A layer of 100 nm of a-Si is also deposited by the same technique. SPR-220 photoresist was spin coated on both sides, and a chromium mask with 10 um window and dividing lines was used to pattern squares of 10 μm in size at the center and divide the wafer into 5×5 mm chips by photolithography. The a-Si and SiNx layers were etched away by reactive-ion etching using CF4 gas. The glass substrate was etched in a 49% HF solution with an etch rate ~1 μm/min until the sphere created by isotropic etching reaches the bottom SiNx layer. The remaining photoresist and a-Si were stripped away by acetone and KOH respectively.

For the two-step etching design, one may apply via spin-coating the electron beam resist (ZEP520) covering the entire chip and perform electron beam lithography to create a patterned aperture smaller than 5 μm in radius at the center of the etched sphere. The chip is then etched again in the HF bath until the second etched sphere reaches the SiNx layer and forms a suspended membrane. Single-layer CVD graphene was grown on copper foil, and could be cut into squares to fit the size of the chip. After spinning on a PMMA support layer, one may use bubbling transfer techniques to isolate the graphene and PMMA from copper. The graphene is then transferred onto the glass chip with a 300 nm aperture into the suspended SiN membrane.

The quality of CVD-grown graphene is discussed in supplemental information and characterized by Raman spectroscopy and its defect concentration is estimated as in Gogneau et al., Surf. Sci. 606, 217-220 (2011). Nanopores are drilled using a focused electron beam on a JEOL 2010F transmission electron microscope operating at 200 kV.

Measurements

The exemplary measurement cell had two chambers of 1 M KCl, 1 mM EDTA solution buffered using 10 mM TrisHCl. Experiments were conducted using a VC100 voltage-lamp amplifier (Chimera Instruments, New York, N.Y.), to apply a bias voltage using Ag/AgCl electrodes and measure ion current through the nanopore. The amplifier applies a fourth order Bessel low-pass filter at 1 MHz. For translocation experiments bias voltages of 200 mV-1 V were applied across the nanopore. For capacitance measurements a triangle wave was applied and the capacitance is estimated from the current variation when the sign of the voltage slope changes, similar to measurements done by Balan et al., Nano Lett. 14, 7215-7220 (2014).

DNA Sequencing with solid state nanopore is hampered today by the high current noise present at the high bandwidths necessary to sequence in a reasonable timeframe (i.e., without slowing down the DNA, or for 10 min full genome).

As shown, these bandwidths the dominant noise come from the chip and amplifier capacitance. The devices provided here enhance the existing nanopores devices designs which in majority are supported by a Si substrate, which limit their minimal capacitance to about 1 pF. This disclosure provides nanopore device composed from insulating layers, e.g., implementation for thin membranes supported by fused silica, although other insulating substrates could be used (PDMS, glass, plastic, photoresists). Because the capacitance is expressed as C=eS/t, thin areas may, in some embodiments, have a surface as small as possible, as an inverted pyramid structure is suited to adapt between the thin areas around the pore and the macro electrode.

Additional Disclosure

Aspect 1. A macromolecule analysis chip, comprising: a glass membrane having a thickness defined between first and second surfaces of the glass membrane, the thickness being in the range of from about 10 micrometers to about 5000 micrometers, the glass membrane further having a first cavity formed in the thickness of the glass membrane, the first cavity having a width that increases along the direction extending from the first surface of the membrane to the second surface of the membrane, a first membrane surmounting at least a portion of the first surface of the glass membrane, the first membrane having a pore formed therethrough, and the pore of the first membrane being in fluid communication with the first cavity of the glass membrane.

The glass membrane is suitably formed from a silicate glass, e.g., a glass based on silicon dioxide. Fused quartz (sometimes termed fused silica glass, vitreous silica), soda-lime glass, sodium borosilicate glass, lead-oxide glass, aluminosilicate glass, and germanium glass are all considered suitable glasses. The glass membrane is suitably planar, e.g., similar to a microscope slide, although this is not a requirement.

The first cavity is suitably at least partially spherical in configuration, e.g., hemispherical. The cavity need not be half-spherical, as it may be a quarter-sphere in configuration or otherwise at least partially spherical. The first cavity may have an effective radius (e.g., R1 as shown in FIG. 1A) of from about 1 to about 1000 micrometers (subject, of course, to the thickness of the glass membrane), e.g., from about 10 to about 900 micrometers, from about 50 to about 800 micrometers, from about 100 to about 700 micrometers, from about 150 to about 600 micrometers, from about 200 to about 550 micrometers, from about 250 to about 500 micrometers, from about 300 to about 450 micrometers, or even from about 350 to about 400 micrometers. The first cavity may also have a radius of, e.g., 5, 10, 15, 20, 25, 30, 35, 40, 45, 50, 55, 60, 65, 70, 75, 80, 85, 90, 95, or even about 100 micrometers. As explained herein, a cavity (whether first or second) formed in the glass membrane may extend such that the volume of the cavity reaches the surface of the glass membrane. In one embodiment, a cavity may be formed such that the cavity reaches a membrane that surmounts a surface of the glass membrane.

It should be understood that the volume of a cavity may have a sphericality to its profile. As one example, the cavity may be spherical (which includes configurations that are not perfectly spherical) or be part of a sphere, e.g., a hemisphere, or even a portion of a sphere that is somewhere between a full sphere and a hemisphere. A cavity may also be a portion of a sphere that is something less than a hemisphere. The form of a cavity may, in some embodiments, be a function of the process by which the cavity was formed, e.g., a wet-etch process using HF as an etchant may give rise to a spherical-shaped cavity formed in the glass membrane.

The first membrane may be formed of a variety of materials. Silicon nitride (SiNx) is considered especially suitable, but is not the exclusive choice of material for the first membrane. Silicon oxide may also be used as the first membrane, in some embodiments. The first membrane suitably has a thickness in the range of from about 1 to about 500 nm, e.g, about 10, 20, 50, 100, 150, 200, 250, 300, 350, 400, 450, or even about 500 nm.

Aspect 2. The chip of aspect 1, wherein the glass membrane has a thickness in the range of from about 10 micrometers to about 1000 micrometers. The glass membrane may have a thickness in the range of from, e.g., from about 150 to 900 micrometers, from about 200 to about 850 micrometers, from about 250 to about 800 micrometers, from about 300 to about 750 micrometers, from about 350 to about 700 micrometers, from about 400 to about 650 micrometers, from about 450 to about 600 micrometers, from about 500 to about 550 micrometers.

Aspect 3. The chip of aspect 2, wherein the glass membrane has a thickness is in the range of from about 200 micrometers to about 500 micrometers.

Aspect 4. The chip of any of aspects 1-3, further comprising a second membrane surmounting at least a portion of the second surface of the glass membrane. The second membrane may be formed from SiNx, but SiNx is not the sole choice for the second membrane. The second membrane suitably has formed therethrough an aperture, the aperture being in fluid communication with the first cavity of the glass membrane.

One such chip is shown in non-limiting FIG. 2A, which shows a first SiN membrane at the lower (first) surface of the glass membrane, and a second SiN membrane at the upper (second) surface of the glass membrane; as shown in this FIG., the cavity formed in the glass membrane becomes wider as one moves on a line from the first surface of the membrane to the second surface.

Aspect 5. The chip of any of aspects 1-4, wherein the first cavity is characterized as being at least partially spherical. The first cavity may be, e.g., hemispherical. Other shapes are suitable, in particular shapes that are narrowed along the direction of the first surface of the membrane toward the second surface.

Aspect 6. The chip of any of aspects 1-5, wherein the first cavity has a characteristic cross-sectional dimension of about the thickness of the glass membrane.

Aspect 7. The chip of any of aspects 1-6, further comprising a second cavity extending at least partially through the thickness of the glass membrane, the second cavity being in fluid communication with the first cavity, and the second cavity optionally being at least partially spherical. One example is provided by FIG. 2D, which FIG. provides a device having a first cavity with radius R1 and a second cavity with radius R2, wherein R2 is suitably smaller than R1.

The ratio of R1 to R2 may in some embodiments be, e.g., from about 1000:1 to 1.01:1, as R2 may be smaller than R1. R1:R2 ratios of from about 1000:1 to 10:1, 750:1 to 50:1, or even 500:1 to 100:1 are all considered suitable. Ratios of 10:1, 9:1, 8:1, 7:1, 6:1, 5:1, 4:1, 3:1, and 2:1 are also considered suitable. R2 may be in the range of, e.g., from about 1 micrometer to about 100 micrometers, from about 1 to about 50 micrometers, from about 2 to about 45 micrometers, from about 3 to about 40 micrometers, from about 4 to about 35 micrometers, from about 5 to about 30 micrometers, from about 6 to about 25 micrometers, from about 7 to about 20 micrometers, from about 8 to about 15 micrometers, or even about 10 micrometers.

Figure 7A:
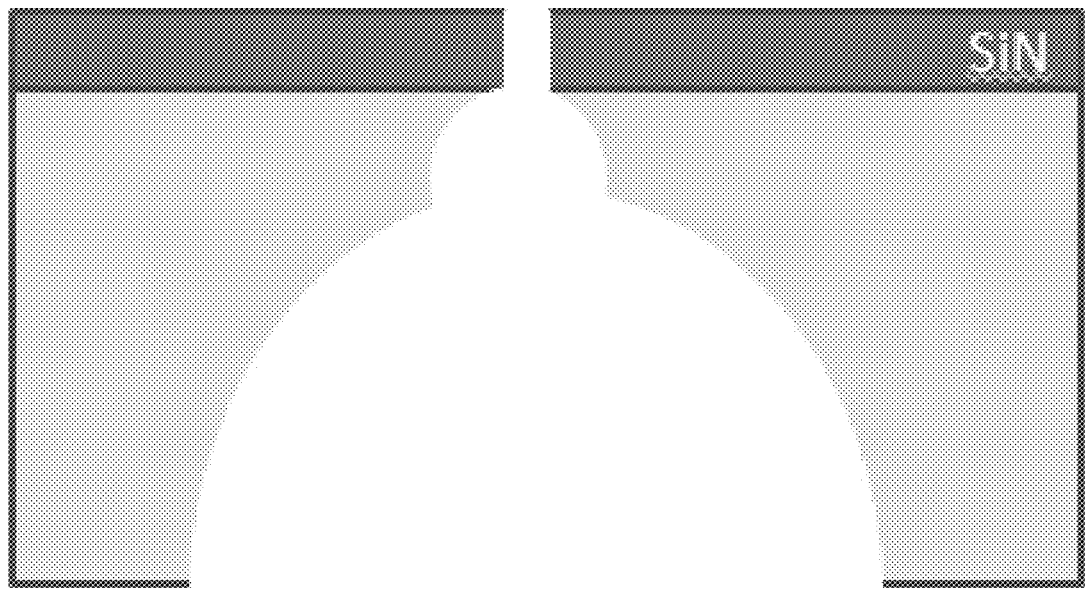
FIG. 7A provides an exemplary cutaway view of a chip according to the present disclosure.

Another example is provided by FIG. 7A, which FIG. provides a device having a first cavity (shown by "1") and a second cavity (shown by "2") formed in a glass substrate. The first surface of the glass substrate is in turn surmounted by a first membrane (SiN, in this instance). The first membrane has a pore formed therethrough, which pore is in fluid communication with the second cavity 2 as well as the first cavity 1 formed in the glass membrane.

Aspect 8. The chip of aspect 7, wherein the second cavity has a characteristic cross-sectional dimension that is less than the corresponding characteristic cross-sectional dimension of the first cavity and wherein the second cavity has a width that increases along the direction extending from the first surface of the membrane to the second surface of the membrane. An exemplary embodiment is provided in FIG. 7A, which provides a device wherein the second cavity has a smaller cross-sectional dimension (e.g., effective diameter) than the corresponding cross-sectional dimension of the first cavity.

Aspect 9. The chip of any of aspects 7-8, wherein the second cavity extends along a line extending from the first surface of the glass membrane to the second surface of the membrane, and wherein the first cavity extends from the second cavity along the line extending from the first surface of the membrane to the second surface of the glass membrane.

Aspect 10. The chip of any of aspects 1-6, wherein the chip has a capacitance of less than about 2 pF, e.g, about 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or even about 0.1 pF.

Aspect 11. The chip of any of aspect 7-9, wherein the chip has a capacitance of less than about 1 pF, e.g., 0.9, 0.8, 0.7, 0.6, 0.5, 0.4, 0.3, 0.2, or even about 0.1 pF.

Aspect 12. The chip of any of aspects 1-11, wherein the pore of the first membrane has a characteristic cross-sectional dimension in the range of from about 1 nm to about 100 nm, e.g., from about 1 to about 50 nm, from about 2 to about 20 nm, or even from about 3 to about 10 nm.

Aspect 13. The chip of aspect 12, wherein the pore of the first membrane has a characteristic cross-sectional dimension in the range of from about 1 nm to about 10 nm, e.g., from about 2 to about 8 nm, from about 3 to about 7 nm, from about 4 to about 6 nm, or even about 5 nm.

Aspect 14. The chip of aspect 12, further comprising an additional membrane disposed on a surface of the first membrane.

Aspect 15. The chip of aspect 14, therein the additional membrane comprises a 2D material. Suitable 2D materials include, $MoS_2$, $WS_2$, graphene, and the like. A 2D material may have a thickness of a single atomic layer. The 2D material may also be conductive or semiconductive in nature.

Aspect 16. The chip of any of aspects 14-15, wherein the additional membrane has a thickness of from about 2 Angstroms to about 20 Angstroms.

Aspect 17. The chip of any of aspects 14-16, wherein the additional membrane has an atomic-level thickness.

Aspect 18. The chip of any of aspects 14-17, wherein the additional membrane comprises $MoS_2$, graphene, $WS_2$, or any combination thereof.

Aspect 19. A method of fabricating an analysis chip, comprising: in a glass membrane having a thickness defined between first and second surfaces of the glass membrane, forming a first cavity in the glass membrane, the first cavity having a width that increases along the direction extending from the first surface of the membrane to the second surface of the membrane.

Figure 7B:
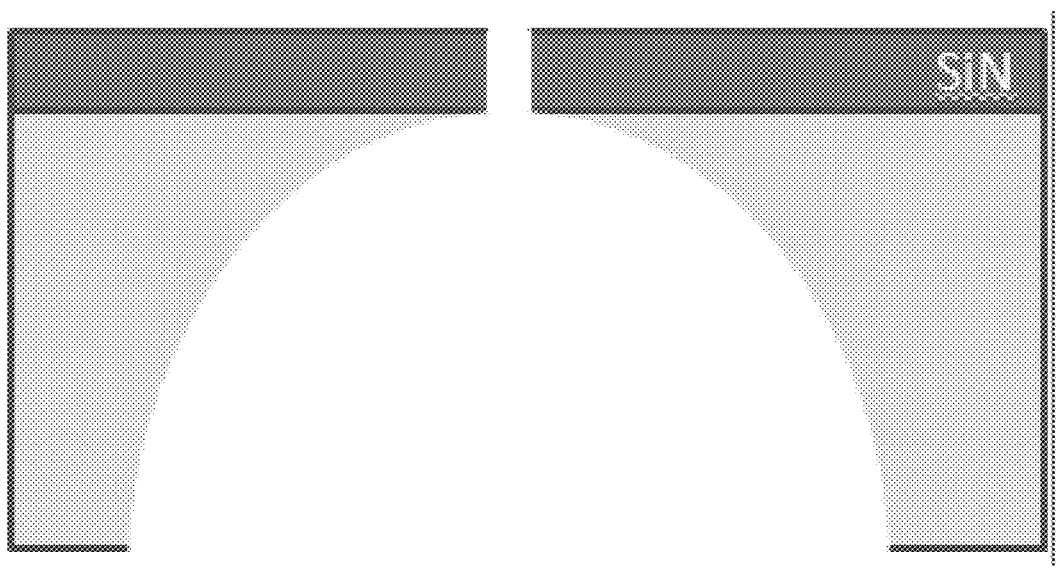
FIG. 7B provides an alternative view of a chip according to the present disclosure.

As shown in, e.g., FIG. 7B, the first cavity may reach the surface of the glass membrane so as to form an aperture in the glass membrane. The aperture in the glass membrane may be, e.g., in the range of from about 1 to about 100 micrometers, and all intermediate values, e.g., 1, 5, 10, 15, 20, 25, 30, 35, 40, 45, 50, 55, 60, 65, 70, 75, 80, 85, 90, 95, or even about 100 micrometers.

Aspect 20. The method of aspect 19, further comprising forming a second cavity in the glass membrane, the second cavity extending at least partially through the thickness of the glass membrane, the second cavity being in fluid communication with the first cavity. As shown in, e.g., FIG. 7A, the second cavity may reach the surface of the glass membrane so as to form an aperture in the glass membrane. The aperture in the glass membrane may be, e.g., in the range of from about 1 to about 100 micrometers, and all intermediate values, e.g., 1, 5, 10, 15, 20, 25, 30, 35, 40, 45, 50, 55, 60, 65, 70, 75, 80, 85, 90, 95, or even about 100 micrometers.

Aspect 21. The method of aspect 20, wherein the second cavity extends along a line extending from the first surface of the membrane to the second surface of the membrane, and wherein the first cavity extends from the second cavity along the line extending from the first surface of the membrane to the second surface of the membrane. One such embodiment is shown in FIG. 2C.

Aspect 22. The method of any of aspects 19-21, wherein the second surface of the glass membrane is surmounted by a first membrane. Suitable first membranes are described elsewhere herein. SiNx is a suitable material for a first membrane, but other materials—in particular those that may exist as free-standing membranes—are also considered suitable.

Aspect 23. The method of aspect 22, further comprising forming an aperture in the first membrane, the aperture being in fluid communication with the first cavity of the glass membrane, and the aperture having a characteristic cross section in the range of from about 1 nm to about 1000 nm, e.g., from about 1 to about 500 nm, from about 2 to about 250 nm, from about 3 to about 100 nm, or even from about 5 to about 50 nm.

Figure 5:
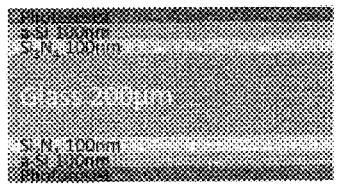
FIG. 5 provides an exemplary fabrication process for a device according to the present disclosure.
Figure 5:
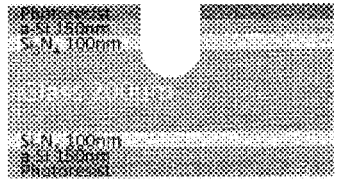
Figure 5:
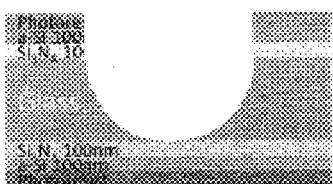
Figure 5:
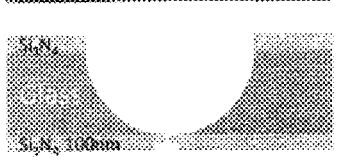

One exemplary fabrication process is provided in FIG. 5. As shown in that FIG., a user may form a workpiece that comprises a glass membrane. The glass membrane may be surmounted by a first membrane; in the non-limiting embodiment of FIG. 5, the glass membrane is surmounted on both surfaces with a layer of $Si_3N_4$ or other suitable membrane material.

The $Si_3N_4$, in turn, may be surmounted by a later of a further material (e.g., a-Si) that may be used as a protection against the etching process applied to the glass; though this is not a requirement. An amount of photoresist is then disposed atop the layers of a-Si. Without being bound to any particular theory, the photoresist may be used to as to afford the user control over the pattern of windows in the layers that surmount the glass membrane.

In a second step, a portion of the photoresist is removed (which may be accomplished in a patterned fashion, using a mask), followed by further material removal to as to expose the glass membrane. The material removal may be effected vie RIE etching, chemical etching, and the like. A wet etch or other process may then be used to form a cavity in the glass membrane, as shown by the third step in FIG. 5. The user may select the etching material and conditions to give rise to the desired cavity configuration. As one example, a user may use a comparatively fast-etching material to form a comparatively wide first cavity, stop the etching, and then perform a second etch to as to form a second cavity in the glass membrane.

In later steps (shown in the final, bottommost step in FIG. 5), the user may remove remaining the photoresist and a-Si, using suitable removal techniques. A user may optionally thin a region of the first membrane surmounting the first surface of the glass membrane (as shown in FIG. 5), and then form a nanopore through the thinned region of the first membrane, e.g., by using a TEM device. Alternatively, a user may form a nanopore though the first membrane without also thinning a region of the membrane through which the pore is formed. The resultant device includes a cavity formed in the glass membrane, the cavity being in fluid communication with a nanopore formed through a membrane that surmounts a surface of the glass cavity.

It should be understood that the various materials and processes described above and in FIG. 5 are non-limiting and are illustrative only. For example, although the fabrication process described above includes the use of a-Si, it should be understood that a-Si is not the exclusive material that can be used as the a-Si is deployed in the example above.

The glass membrane (e.g., fused silica) may have a thickness in the range of from about 10 micrometers to about 1000 micrometers, and all intermediate values. The first membrane ($Si_3N_4$) may have a thickness in the range of from about 1 to about 500 nm. The optional protection layer (a-Si, in this instance) may have a thickness of from about 1 to about 500 nm.

Aspect 24. A method, comprising: using a chip according to any of aspects 1-18 to perform structural analysis of a macromolecule.

Suitable macromolecules include, e.g., DNA, RNA, oligomers, and the like. Biomolecules, such as single-stranded DNA, are considered especially suitable.

The structural analysis may be performed by, e.g., effecting motion of a macromolecule through the cavity/cavities and pore of a device according to the present disclosure and monitoring one or more signals related to the motion of the macromolecule. As one example, a user may translocate a macromolecule across or through a chip via application of a gradient, e.g., a chemical, magnetic, electrical, or other gradient. A user may then monitor a signal, e.g., via electrodes capable of electronic communication with the pore, that is related to the translocation of the macromolecule through the pore. By correlating signals to one or more structural features of the macromolecule (e.g., amino acid, base), a user may obtain structural information about a given macromolecule.

In some embodiments, a device according to the present disclosure is placed into fluid communication with a supply of sample, e.g., a supply of macromolecules. A gradient is applied, and macromolecules are then translocated through the pore of the device, and one or more signals related to the passage of a macromolecule through the pore are then monitored. A supply of sample may be placed into fluid communication with a plurality of devices according to the present disclosure so as to allow arrayed or parallel, simultaneous analysis of many macromolecules.

As but one example, a user may translocate a macromolecule through a device according to any of the foregoing aspects, and collect a signal (e.g., an electrical signal) related to that translocation. The user may further correlate that signal to one or more structural features of the macromolecule.

It should be understood that a device according to the present disclosure may include multiple cavities and multiple pores. As one example, a device may include a plurality of glass cavities, each cavity being in fluid communication with a nanopore (formed in a membrane that surmounts the glass membrane) that is individually addressable, e.g., a device in which each of three cavities formed in a glass membrane is in fluid communication with a nanopore that is in fluid communication with only one cavity associate with that nanopore and no other cavities. Alternatively, a cavity may be in fluid communication with two or more nanopores.

The following provides additional explanation of the attached drawings.

FIG. 1A provides a schematic of a glass chip with a suspended silicon nitride membrane positioned between two chambers of electrolyte solution with bias voltage applied across the membrane. Not shown in FIG. 1A is the pore that may be formed through the SiNx membrane, in register with the cavity formed in the glass membrane.

FIG. 1B provides an optical image of the glass wafer of FIG. 1A, containing several 5×5 $mm^2$ glass chips (left) and an optical micrograph of the center area of the glass chip (right) wherein the SiNx membrane is freestanding at the center of glass isotropically etched away forming a hollow sphere (grey circle shadow).

FIG. 1C provides a schematic of the glass and the membrane manufacturing process for the device of FIG. 1A and FIG. 1B.

As shown, a workpiece may be formed with a glass membrane having an exemplary thickness in the range of from about 200 to about 500 micrometers. This thickness is illustrative only, and glass membranes may have a thickness in the range of from less than about 100 micrometers up to 600, 700, 800, 900, or even 1000 micrometers.

The thicknesses of the SiNx (100 nm) and a-Si layers (100 nm) are also illustrative only and are not limiting. The SiNx layer may have a thickness of, e.g., from about 1 or 5 nm up to 100, 200, 300, 400, 500, 600, 700, 800, 900, or even 1000 nm. Similarly, the a-Si layer may also have a thickness in the range of from about 1 or 5 nm up to 100, 200, 300, 400, 500, 600, 700, 800, 900, or even 1000 nm. The thickness of the photoresist may vary according to the needs of the user as well as the parameters of a particular process.

As shown in FIG. 1C, the layers above the glass membrane may be formed of materials that are etched selectively, relative to the glass. In this way, a user may—as shown in FIG. 1C—open a window in the upper layers to as to afford access to the glass. Once the glass is exposed, the user may then effect an etching process on the glass (shown pictorially in FIG. 1C) to form a cavity in the glass. The cavity may be formed so as to reach the membrane (SiNx, in this instance) that surmounts the non-accessed surface of the glass membrane. Further steps—described herein—may then be used to form a pore through the membrane that surmounts the bottom surface of the glass, which pore is in register with the cavity of the glass membrane.

In the example of FIG. 1C, on both sides of a 200-500 μm thick glass was deposited 100 nm of SiNx and 100 nm a-Si. Spin-coating was used to apply 10 μm of SPR-200 photoresist on both sides. Squares of 25 μm in size were patterned using photolithography at the center, and then the a-Si and SiNx layers are removed with reactive ion etching. Glass was then etched in a 49% HF solution until the sphere created by isotropic etching reaches the bottom of the SiNx layer. The remaining photoresist and a-Si were stripped away, forming the aperture in the glass chip covered by the silicon nitride membrane.

FIG. 2A provides a schematic of a glass chip with silicon nitride membrane in the center, with an optional insulator (in this case a silicone elastomer, Kiwk-Cast™) applied on top to provide insulation. The different areas contributing to the chip capacitance are shaded.

FIG. 2B provides a corresponding circuit diagram for the device of FIG. 2A, wherein $C_{mem}$, $C_1$, $C_{rest}$ are capacitances of the boxed areas, respectively. FIG. 2C provides a bar graph of chip capacitance for glass thickness values of 200, 300, 400, and 500 μm, showing relative contributions from regions $C_{rest}$, $C_1$ and $C_{mem}$, and the inset is the minimum capacitance as a function of glass thickness, with the units in the inset being the same as in the main FIG. 2B.

FIG. 2D provides a schematic of a glass chip device produced by a two-step etching that gives rise to first and second cavities formed in the glass substrate. The first of the two cavities has a radius R1, and the second cavity has a radius R2, as shown in FIG. 2D. The different areas contributing to the chip capacitance are again shaded/boxed. $C_{mem}$ is the capacitance of the membrane, $C_1$ is the capacitance of the spherical area with radius R1, $C_2$ is the capacitance of the spherical area with radius R2, and $C_{rest}$ is the capacitance of the rest of the chip.

Without being bound to any particular theory, the two-cavity configuration may be formed by forming a first cavity that does not reach the bottom surface (as illustrated in FIG. 2D) of the glass membrane. Following formation of the first cavity, the second cavity is formed, e.g., via a second etching process. The second cavity may be formed such that the cavity reaches the membrane (SiNx, in this instance) that surmounts the non-accessed surface of the glass membrane. Further steps—described herein—may then be used to form a pore through the membrane that surmounts the bottom surface of the glass, which pore is in register with the cavity of the glass membrane.

It should be understood that the first and second cavities may be coaxial with one another, but this is not a requirement. Likewise, the first cavity, second cavity, and pore formed in the first membrane may be coaxial with one another, though this too is not a requirement, as one or more of the foregoing may be offset somewhat from one or more of the others.

FIG. 2E provides a corresponding capacitor circuit diagram for the device of FIG. 2D, wherein $C_{mem}$, $C_1+C_2$, $C_{rest}$ are capacitances of the boxed areas, respectively. FIG. 2F provides a bar graph of the chip capacitance for glass thickness of 200, 300, 400, and 500 μm, respectively, showing relative contributions from regions $C_{rest}$, $C_1+C_2$ and $C_{mem}$. The inset is the minimum capacitance as a function of glass thickness. The units are the same as the main FIG. 2F.

FIG. 3A provides an illustration of using 2D materials, such as graphene or $MoS_2$, on a membrane-on-glass chip, thus providing a sub-1 pF capacitance platform. As shown in FIG. 3A, a glass membrane may have a cavity formed therein. A first membrane (SiNx, in this instance) surmounts the glass membrane, with a pore formed in the first membrane being in fluid communication with (and in register with) the cavity of the glass membrane. A 2D material (graphene and $MoS_2$ are non-limiting examples of such materials) may be disposed so as to surmount the first membrane. The 2D material may be a conductive or semiconductive material.

A pore (not shown in FIG. 3A) may be formed in the 2D material, the pore suitably being in register with the pore of the first membrane. The pore formed in the 2D material may have a cross-sectional dimension (e.g., diameter) that is less than or about equal to the corresponding dimension of the pore formed in the first membrane.

As one example, the pore formed in the first membrane may have a diameter of about 200 nm. The pore formed in the 2D material that surmounts the first membrane may have a diameter of about 10 nm.

FIG. 3B provides a SEM image of a graphene sheet covering the 300-nm-large aperture in the suspended SiNx membrane. The darker area is the circular SiNx membrane, and graphene is covering most of the area of the SiNx membrane, including the aperture at the center. The inset is the enlarged image of the aperture with graphene suspended on top. The white flakes around the suspended graphene area (circular dark area in the center) are residual PMMA after transfer.

FIG. 4A provides the measured capacitance, $C_{chip}$, of exemplary glass chips produced by two-step etching (FIG. 2D) as a function of SiNx membrane radius (μm). The dashed line is $C_{chip}$ estimated from the model in FIG. 2F. The glass chip thickness was 300 μm and the SiNx membrane thickness was 100 nm.

FIG. 4B provides measured ion current temporal traces for several glass chips with capacitances $C_{chip}$=0.69, 0.73, 1.1 pF, and 1.65 pF showing an amplifier-limited noise. A current trace from a 12 pF is shown for comparison.

FIG. 4C provides a current vs. time trace of 3 kbp (kilo base pairs) dsDNA segments translocating through one of the devices. The red trace (between the white lines) is filtered at 100 kHz, and the blue trace (above and below the white lines) is filtered at 1 MHz. The inset is a TEM image of a nanopore drilled with focused electron beam in the TEM.

FIG. 4D provides details of events recorded with the disclosed devices having lengths from 0.5 ms to 10 ms from FIG. 3D.

FIG. 5 provides an exemplary fabrication process for a device according to the present disclosure. (FIG. 5 is described in additional detail elsewhere herein.)

Figure 6:
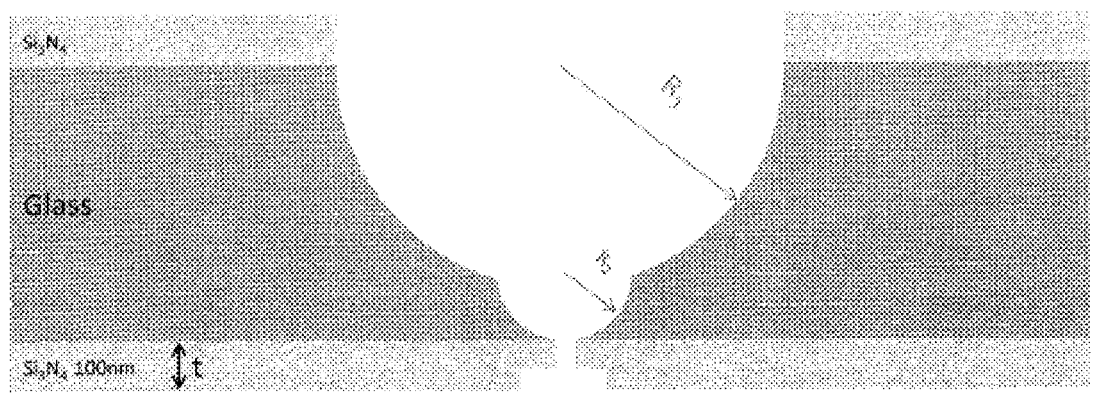
FIG. 6 provides an illustrative chip according to the present disclosure.

FIG. 6 provides an illustrative chip according to the present disclosure.

FIG. 7A provides an exemplary cutaway view of a chip according to the present disclosure. As shown, a chip may comprise a pore-bearing membrane (SiNx, in this instance) atop a glass substrate, wherein the glass substrate has etched therein two cavities which may, in some embodiments, provide a so-called "snowman" profile. The pore of the membrane is placed in fluid communication with the cavities of the glass substrate.

FIG. 7B provides an alternative view of a chip according to the present disclosure. As shown, a chip may comprise a pore-bearing membrane (SiNx, in this instance) atop a glass substrate, wherein the glass substrate has etched therein a cavity. The pore of the membrane is placed in fluid communication with the cavity of the glass substrate.

Figure 9:
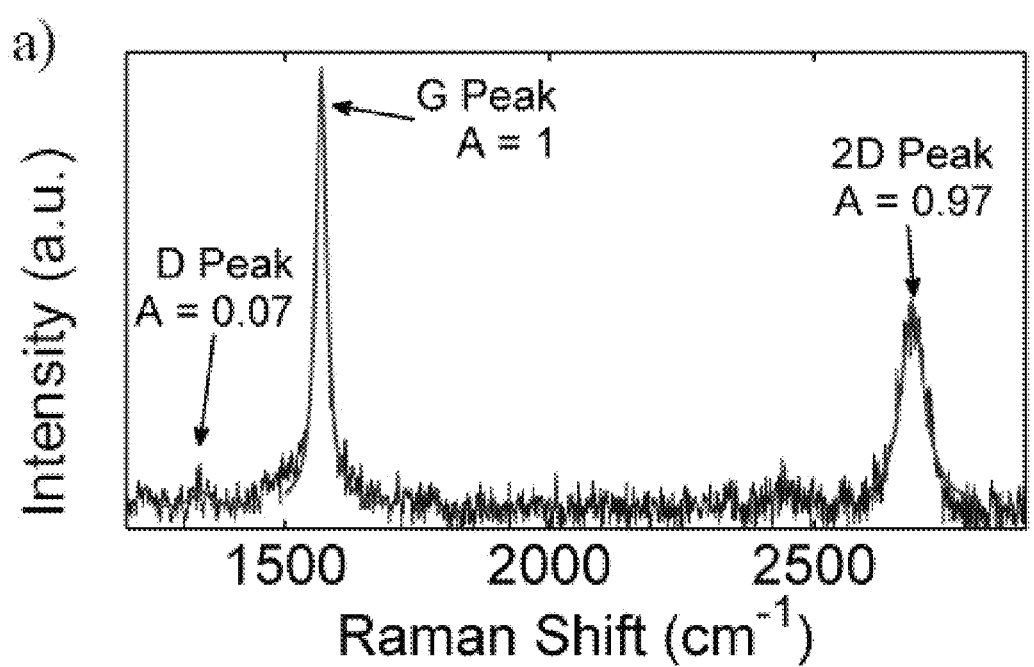
FIG. 9 provides a representative Raman spectrum acquired on a graphene sample transferred to a SIN membrane. The integrated intensities of the peaks D, G, and 2D, normalized to the intensity of the G peak is also presented (A=0.07, 1, 0.97 respectively for the D,G and 2D peaks.

Defect spacing can be estimated from the Raman spectra. In FIG. 9 is presented one of the characteristic Raman spectra from the cartography done on one generic graphene sample after transfer to the SiN suspended membrane. The background coming from the SiN membrane is already subtracted. One may identify the Raman signature of graphene (the peak G at 1580 $cm^{-1}$ at 2D at 2680 $cm^{-1}$ A faint D peak, defect activated, can be seen around 1340 $cm^{-1}$. Its integrated amplitude represents only 5% to 10% of the amplitude of the amplitude of the G peak.

SUMMARY

Provided here is, inter alia, an integrated process for producing membranes on glass chips with sub-1 pF capacitance, the use of which has been demonstrated in DNA translocation experiments. To achieve DNA sequencing using solid-state nanopores without slowing down the molecules, on may measure the ionic current at frequencies close to 20 MHz. Other biomolecules sensing applications utilizing nanopores also require to be performed at high bandwidth with enhanced signal to noise ratio to differentiate finer features of the biomolecules. But to achieve this goal requires devices with reduced capacitances. The present disclosure presents significant improvement in reducing the chip capacitance by substituting glass for silicon as a substrate. One-step fabrication process may produce sub-2 pF capacitance and further sub-1 pF capacitance was realized by an improved two-step design, resulting in a low-noise device for biomolecules detection demonstrated by DNA translocation experiments. The lowered noise level and the ease of production and cleaning make these glass chips superior substitutes for conventional silicon chips. The disclosed versatile platform may also be used to suspend 2D materials to achieve higher signal to noise levels in various nanoelectronics and biomolecule detection applications.

What is claimed:

1. A macromolecule analysis chip, comprising:
a glass membrane having a thickness defined between first and second surfaces of the glass membrane,
the thickness being in the range of from about 10 micrometers to about 5000 micrometers,
the glass membrane further having a first cavity formed in the thickness of the glass membrane,
the first cavity having a width that increases along the direction extending from the first surface of the membrane to the second surface of the membrane,
a first membrane surmounting at least a portion of the first surface of the glass membrane,
the first membrane having a pore formed therethrough, and
the pore of the first membrane being in fluid communication with the first cavity of the glass membrane.

2. The chip of claim 1, wherein the glass membrane has a thickness is in the range of from about 100 micrometers to about 1000 micrometers.

3. The chip of claim 1, further comprising a second membrane surmounting at least a portion of the second surface of the glass membrane.

4. The chip of claim 1, wherein the first cavity is characterized as being at least partially spherical.

5. The chip of claim 1, wherein the first cavity has a characteristic cross-sectional dimension of about the thickness of the glass membrane.

6. The chip of claim 1, further comprising a second cavity extending at least partially through the thickness of the glass membrane, the second cavity being in fluid communication with the first cavity, and the second cavity optionally being at least partially spherical.

7. The chip of claim 6, wherein the second cavity has a characteristic cross-sectional dimension that is less than the corresponding characteristic cross-sectional dimension of the first cavity and wherein the second cavity has a width that increases along the direction extending from the first surface of the membrane to the second surface of the membrane.

8. The chip of claim 6, wherein the second cavity extends along a line extending from the first surface of the glass membrane to the second surface of the membrane, and wherein the first cavity extends from the second cavity along the line extending from the first surface of the membrane to the second surface of the glass membrane.

9. The chip of claim 6, wherein the chip has a capacitance of less than about 1 pF.

10. The chip of claim 1, wherein the pore of the first membrane has a characteristic cross-sectional dimension in the range of from about 1 nm to about 100 nm.

11. The chip of claim 10, further comprising an additional membrane disposed on a surface of the first membrane.

12. The chip of claim 11, therein the additional membrane comprises a 2D material.

13. The chip of claim 11, wherein the additional membrane has a thickness of from about 2 Angstroms to about 20 Angstroms.

14. The chip of claim 11, wherein the additional membrane has an atomic-level thickness.

15. A method of fabricating an analysis chip, comprising:
in a glass membrane having a thickness defined between first and second surfaces of the glass membrane,
forming a first cavity in the glass membrane, the first cavity having a width that increases along the direction extending from the first surface of the membrane to the second surface of the membrane.

16. The method of claim 15, further comprising forming a second cavity in the glass membrane, the second cavity extending at least partially through the thickness of the glass membrane, the second cavity being in fluid communication with the first cavity.

17. The method of claim 16, wherein the second cavity extends along a line extending from the first surface of the membrane to the second surface of the membrane, and wherein the first cavity extends from the second cavity along the line extending from the first surface of the membrane to the second surface of the membrane.

18. The method of claim 15, wherein the second surface of the glass membrane is surmounted by a first membrane.

19. The method of claim 18, further comprising forming an aperture in the first membrane, the aperture being in fluid communication with the first cavity of the glass membrane, and the aperture having a characteristic cross section in the range of from about 1 nm to about 1000 nm.

20. A method, comprising:
with a chip comprising:
a glass membrane having a thickness defined between first and second surfaces of the glass membrane,
the thickness being in the range of from about 10 micrometers to about 5000 micrometers,
the glass membrane further having a first cavity formed in the thickness of the glass membrane,
the first cavity having a width that increases along the direction extending from the first surface of the membrane to the second surface of the membrane,
a first membrane surmounting at least a portion of the first surface of the glass membrane,
the first membrane having a pore formed therethrough, and
the pore of the first membrane being in fluid communication with the first cavity of the glass membrane,
translocating a macromolecule through the pore of the first membrane; and
monitoring a signal related to the translocation.

* * * * *